(12) United States Patent
Baxter et al.

(10) Patent No.: US 6,702,813 B1
(45) Date of Patent: *Mar. 9, 2004

(54) APPARATUS AND METHOD FOR MINIMALLY INVASIVE SURGERY USING ROTATIONAL CUTTING TOOL

(75) Inventors: Jeffrey W. Baxter, San Jose, CA (US); John Davis, Mountain View, CA (US)

(73) Assignee: Origin Medsystems, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/022,680

(22) Filed: Dec. 17, 2001

Related U.S. Application Data

(63) Continuation of application No. 09/522,254, filed on Mar. 9, 2000.

(51) Int. Cl.[7] .................................................. A61B 18/12
(52) U.S. Cl. ............................ 606/49; 606/41; 606/45; 606/48
(58) Field of Search ............................. 606/32, 39, 41, 606/45, 48–50, 167, 180

(56) References Cited

U.S. PATENT DOCUMENTS

| | | | |
|---|---|---|---|
| 3,945,375 A | * | 3/1976 | Banko ........................ 606/49 |
| 5,122,138 A | | 6/1992 | Manwaring |
| 5,133,725 A | | 7/1992 | Quadri |
| 5,190,541 A | | 3/1993 | Abele et al. |
| 5,217,479 A | * | 6/1993 | Shuler ........................ 606/180 |
| 5,282,799 A | | 2/1994 | Rydell |
| 5,304,190 A | | 4/1994 | Reckelhoff et al. |
| 5,352,222 A | | 10/1994 | Rydell |
| 5,356,408 A | | 10/1994 | Rydell |
| 5,437,630 A | * | 8/1995 | Daniel et al. ................ 604/22 |
| 5,445,638 A | | 8/1995 | Rydell et al. |
| 5,462,546 A | | 10/1995 | Rydell |
| 5,498,258 A | | 3/1996 | Hakky et al. |
| 5,527,331 A | | 6/1996 | Kresch et al. |
| 5,540,685 A | | 7/1996 | Parins et al. |
| 5,573,424 A | | 11/1996 | Poppe |
| 5,766,166 A | | 6/1998 | Hooven |
| 5,810,809 A | * | 9/1998 | Rydell ........................ 606/46 |
| 5,817,013 A | | 10/1998 | Ginn et al. |
| 5,860,975 A | | 1/1999 | Goble et al. |
| 5,891,141 A | | 4/1999 | Rydell |
| 5,951,549 A | | 9/1999 | Richardson et al. |
| 5,954,720 A | | 9/1999 | Wilson et al. |

\* cited by examiner

*Primary Examiner*—Roy D. Gibson
*Assistant Examiner*—Henry M. Johnson, III
(74) *Attorney, Agent, or Firm*—Blakely, Sokoloff, Taylor & Zafman LLP

(57) ABSTRACT

An apparatus and method for minimally invasive surgery using a cutting tool with rotational cutting edges. The surgical instrument includes a tube having a distal end and a cutting edge at the distal end. A handle is attached to the proximal end of the tube. Within the tube is a shaft having a longitudinally extending blade at its distal end that is adjacent to the distal end of the tube. The blade is revolvable about the longitudinal axis of the instrument to provide rotational cutting action. One or both of the blade and the cutting edge on the tube can be electrically energized to provide for electrocauterization of the body tissue being cut.

18 Claims, 8 Drawing Sheets

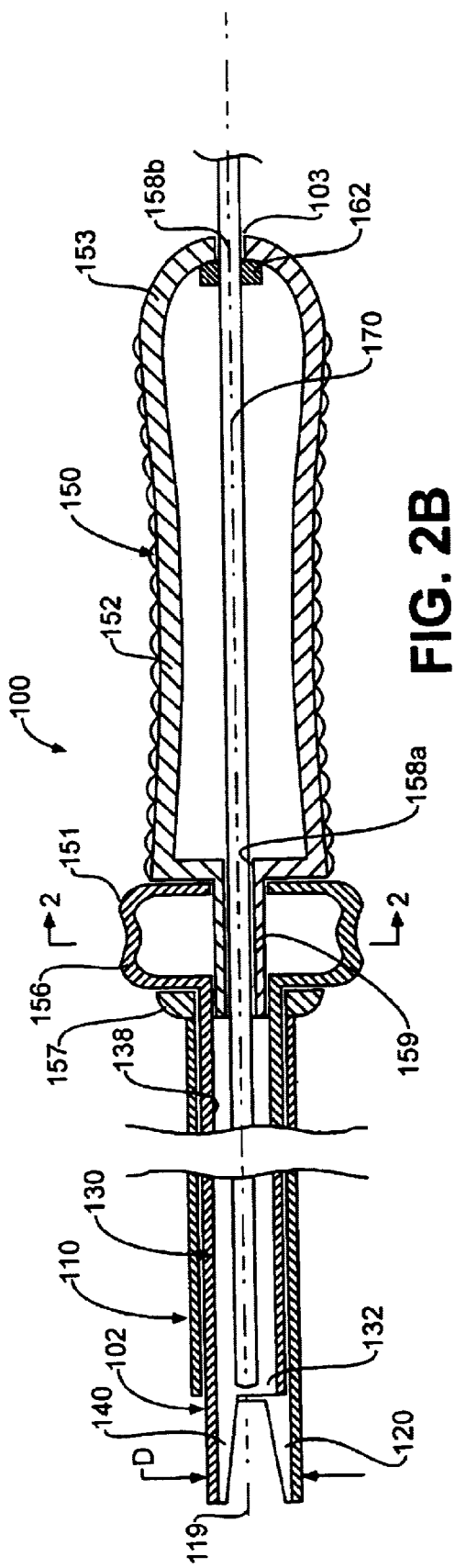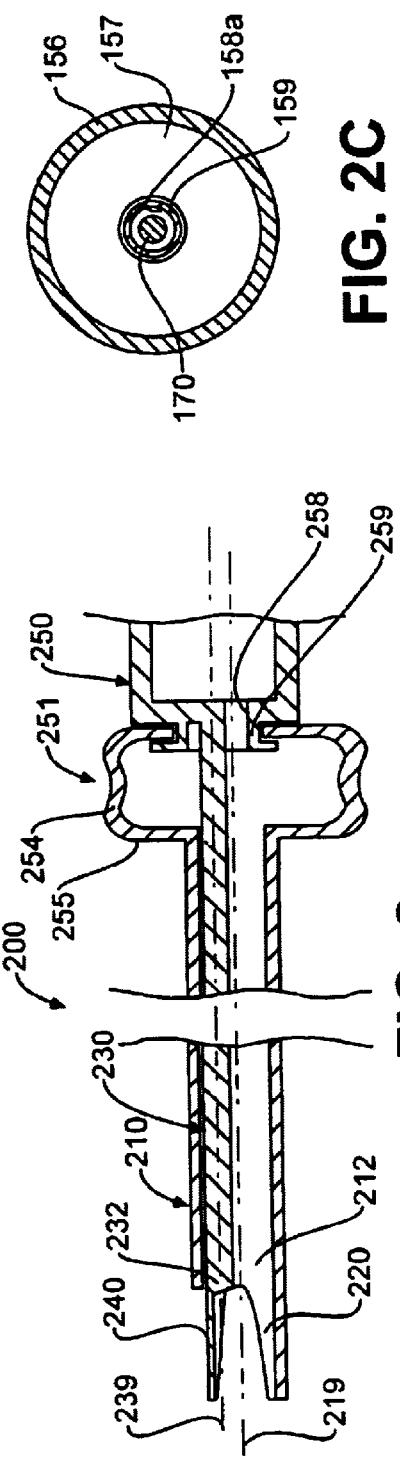

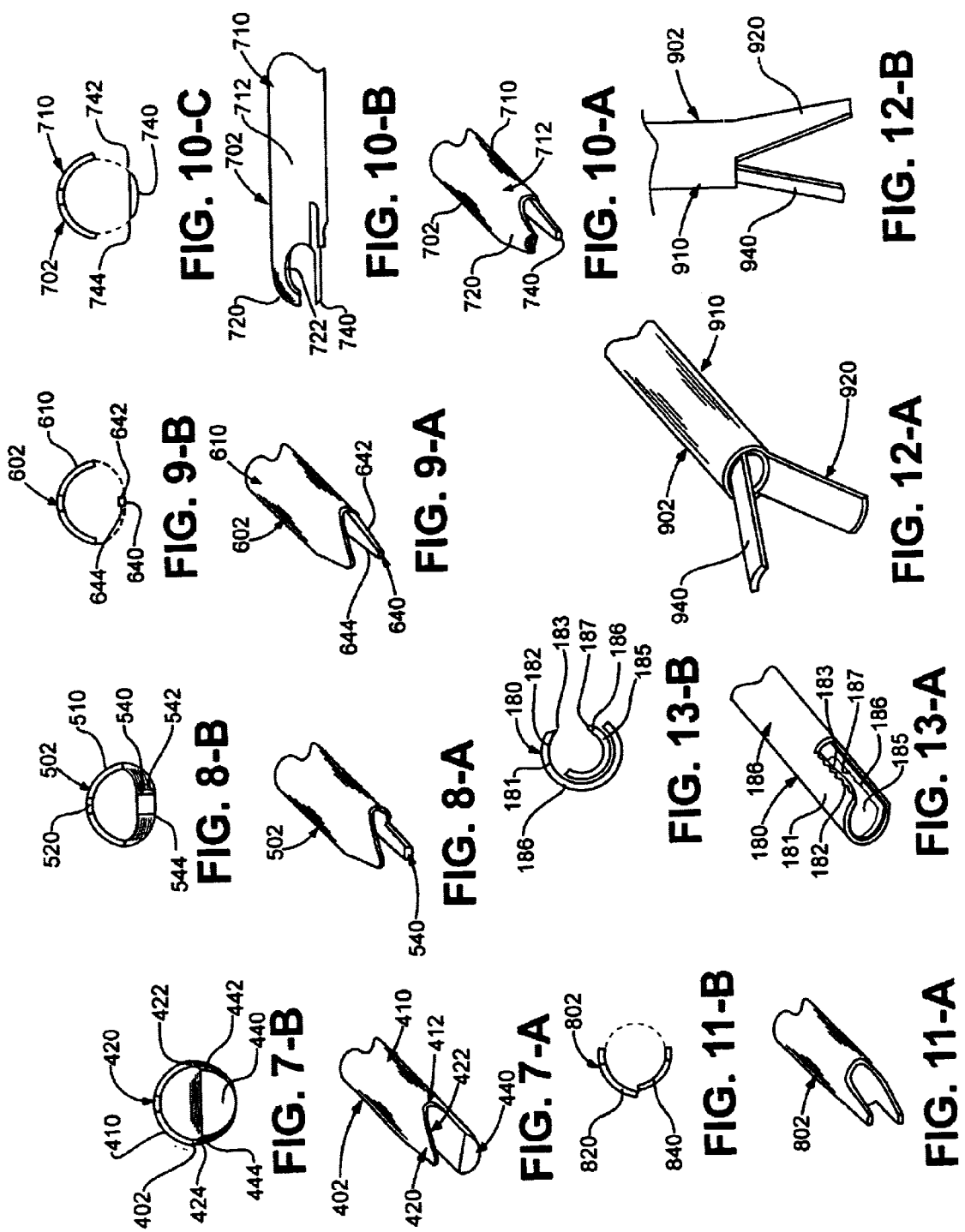

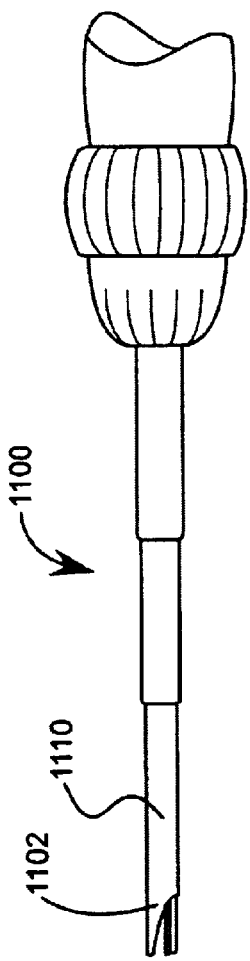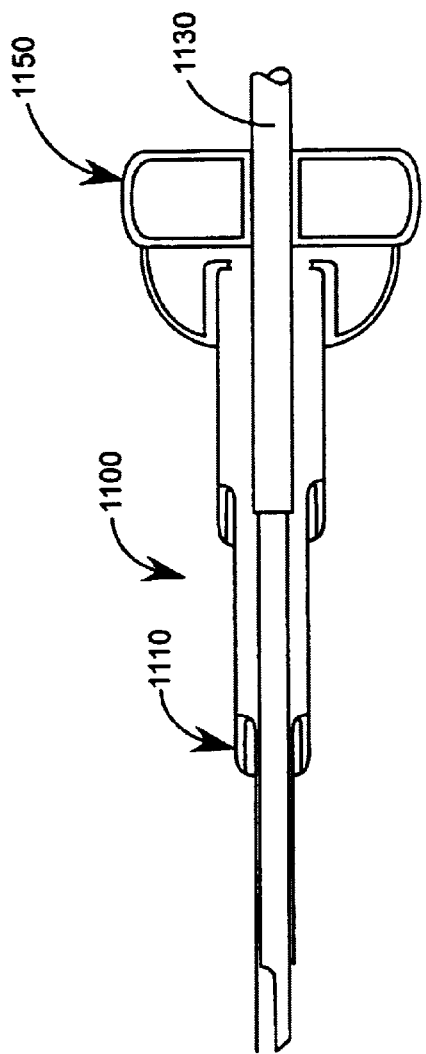
FIG. 17
FIG. 18

APPARATUS AND METHOD FOR MINIMALLY INVASIVE SURGERY USING ROTATIONAL CUTTING TOOL

This is a continuation of application with Ser. No. 09/522,254 filed Mar. 9, 2000.

FIELD OF THE INVENTION

The invention relates generally to minimally invasive surgical tools and techniques and, particularly, to a method and apparatus for cutting body tissue using a bipolar or monopolar electrocautery tool with rotational cutting blades.

BACKGROUND OF THE INVENTION

Minimally invasive surgery such as laparoscopic, endoscopic, hysteroscopic, and arthroscopic surgery is becoming more widely used because it is less traumatic to the patient, generally involves less hospitalization time, less discomfort and less risk to the patient, and can be less costly than traditional open surgery. A minimally invasive surgical procedure is typically performed by making a small incision in the patient which provides access to the area to be treated. A trocar sheath may be inserted in the incision and an airtight seal around the trocar established. The area in the body which is to be treated may be dissected from surrounding tissue by a dissecting tool such as a balloon dissection tool. The dissecting tool is then removed and an elongated surgical tool is inserted through the trocar sheath. Access to the area to be treated may be through one or more trocar sleeves which may be configured to permit the slidable insertion of the endoscopes and surgical instruments without compromising the airtight seal around the trocar sheath.

Minimally invasive surgery is generally performed using elongated instruments slidably inserted through the trocar sleeves, or if the surgery is performed in a naturally occurring body cavity, such as the uterus, the instruments may be inserted through a relatively narrow body orifice such as the cervix. In any event, the operator must perform the surgical manipulations using a tool such as a scalpel or a needle gripper on the end of the elongated surgical instrument. The tool is remotely located from the operator's hands and confined within a relatively small cavity created for the operation. The elongated surgical tool is often endoscopic, i.e., it includes a camera by which the surgeon can observe the area in the body that is to be treated.

FIG. 1 shows prior art pivoting scissors 190 that can be used for surgery. Pivoting blades 192 and 194 of scissors 190 are pivotally attached to an elongated shaft 196 at a pivot point 198. The scissors 190 have a width W when blades 192 and 194 are fully open. The pivoting scissors 190 can be controlled by cables (not shown) that extend through shaft 196. The cables are connected to a pistol grip 191 at the opposite end of shaft 196 that has a lever 193 that is squeezed by the operator. The lever 193 has a lever arm which produces a magnification of the force applied by the operator at the pistol grip 191 and transmitted through the cables to the blades 192 and 194. The pivoting scissors design of FIG. 1 does not provide an opening or a lumen through shaft 196 for an auxiliary instrument such as an endoscope or an irrigation or suction cannula. Thus, pivoting scissors 190 generally do not allow additional instruments to be used through the same incision.

The surgical manipulations must be performed while observing the procedure with an endoscope or other imaging device. The imaging device may be inserted through a separate trocar into the distal cavity. Alternatively, the endoscope may be contained within a surgical tube which also contains surgical instruments. The image from the endoscope is often displayed on a video screen and generally results in an image having little or no depth perception.

One example of an increasingly common minimally invasive surgical procedure involves the "harvesting" of a saphenous vein as part of a heart bypass operation. The saphenous vein can be removed from the leg of a heart bypass patient and then used on the heart to provide the bypass vessels. One method of harvesting a saphenous vein involves making an incision along nearly the entire length of the patient's leg and then removing the saphenous vein by open surgery. This technique can create great discomfort to the patient and increase the risk of complications because of the length of the incision and the open surgery. Also, after such a surgery, the time required for the patient to heal is relatively long.

Another technique commonly used for saphenous vein harvesting involves a minimally invasive procedure that requires two incisions; the first incision being either at the knee area or the ankle area, and the second being at the top of the patient's leg near the groin area. Through one incision, the surgeon inserts a first instrument such as the elongated scissors shown in FIG. 1, and through the other incision, the surgeon inserts a second instrument such as an elongated clamp or a ligating tool. After inserting the two instruments, the surgeon holds one instrument in one hand and the other instrument in the other hand. The surgeon then simultaneously manipulates the instruments to perform the surgical procedure. For instance, the surgeon holds a piece of tissue such as a blood vessel with the clamp, and then cuts the blood vessel with the scissors. This technique, even though it is less invasive than an open incision, is cumbersome for the surgeon to accomplish because the surgeon must manipulate two separate instruments from two different directions or positions.

Also, the two-incision technique is difficult because the surgeon must observe the instruments and tissue in the body cavity from two different directions. When each instrument is accompanied by an endoscope, each endoscope provides an image of the end of the other tool as it moves toward the endoscopic lens from the opposite direction. Even in a single-tool procedure in which the elongated surgical instrument is inserted through the first incision and an endoscope is inserted through the second incision, the endoscope provides an image of the end of the elongated surgical instrument as the surgical instrument is moving toward the endoscope. The surgeon must interpret this counter-intuitive image while manipulating the surgical instrument.

When a saphenous vein is harvested using any of the aforementioned techniques, the main vessel that will be removed must be separated from tributary vessels that branch off the saphenous vein along its length. Before the vessels are cut, they are typically ligated by applying a clip, for example. After the tributaries are cut away from the saphenous vein, they must be permanently closed. This can be accomplished by suturing, clipping, or cauterizing. Each of these ligation techniques requires a separate step, which increases the time required for the surgery.

Surgical procedures can be improved so as to decrease patient discomfort and hospitalization time by techniques that combine the cutting and ligating or cauterizing procedures. One such technique is electrocautery. An electrocautery tool typically includes a scalpel or the blades of scissors that are electrically energized. Electrocautery can be used to simultaneous cut and cauterize tissue.

Methods for improving minimally invasive surgical procedures include decreasing the size of the instrument or performing the procedure through fewer incisions. Decreasing the size of the instrument or reducing the number of incisions reduces the damage caused to the patient's body and tissues, thus reducing the time required for healing.

SUMMARY OF THE INVENTION

An embodiment of the present invention includes a surgical instrument having a tube and a shaft within the tube. The tube and the shaft each have a distal end and a proximal end. The distal end of the tube includes a cutting edge, and the distal end of the shaft includes a blade. Either the blade or the shaft is rotatable with respect to the other such that the blade cooperates with the cutting edge to cut body tissue.

BRIEF DESCRIPTION OF THE DRAWINGS

FIG. 2B is a cross sectional view of the surgical instrument of FIG. 2A;

FIG. 2C is a cross sectional view of the surgical instrument of FIG. 2B taken along line 2—2 of FIG. 2B;

FIG. 3 is a partial cross sectional view of a surgical instrument in accordance with an alternate embodiment of the invention;

FIG. 7A is a partial perspective view of rotational cutting blades of one embodiment of the invention;

FIG. 7B is an end view of the rotational cutting blades of FIG. 7A;

FIG. 8A is a partial perspective view of rotational cutting blades of another embodiment of the invention;

FIG. 8B is an end view of the rotational cutting blades of FIG. 8A;

FIG. 9A is a partial perspective view of rotational cutting blades of another embodiment of the invention;

FIG. 9B is an end view of the rotational cutting blades of FIG. 9A;

FIG. 10A is a partial perspective view of rotational cutting blades of another embodiment of the invention;

FIG. 10B is a side view of the rotational cutting blades of FIG. 10A;

FIG. 10C is an end view of the rotational cutting blades of FIG. 10A;

FIG. 11A is a partial perspective view of rotational cutting blades of another embodiment of the invention;

FIG. 11B is an end view of the rotational cutting blades of FIG. 11A;

FIG. 12A is a partial perspective view of rotational cutting blades of another embodiment of the invention;

FIG. 12B is a side view of the rotational cutting blades of FIG. 12A;

FIG. 13A is a partial perspective view of rotational cutting blades of another embodiment of the invention;

FIG. 13B is an end view of the rotational cutting blades of FIG. 13A;

FIG. 17 is a side view of a surgical instrument of another embodiment of the invention; and FIG. 18 is a cross sectional view of the surgical instrument of FIG. 17.

DETAILED DESCRIPTION

Figure 2A:
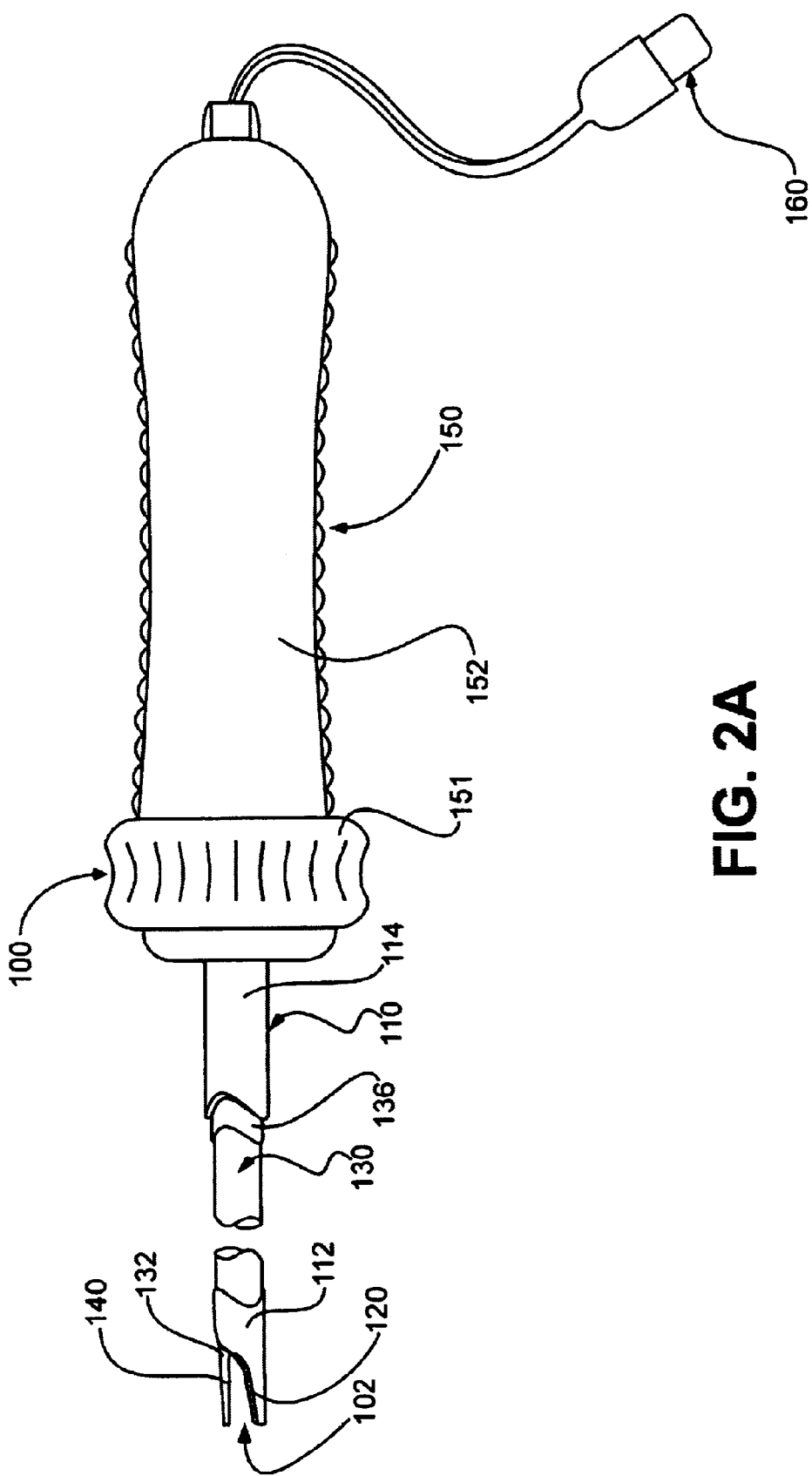
FIG. 2A is a side elevational view of a surgical instrument in accordance with one embodiment of the invention.

FIG. 2A shows an embodiment of a surgical instrument 100 of the invention. Surgical instrument 100 includes a tube 110 and a shaft 130. Tube 110 has a distal end 112 and a proximal end 114. Similarly, shaft 130 includes a distal end 132 and a proximal end (not shown). Distal end 112 of tube 110 includes an outer blade 120 extending longitudinally therefrom. Distal end 132 of shaft 130 includes an inner blade 140 extending longitudinally therefrom. Shaft 130 is rotatably disposed within tube 110 such that inner blade 140 is revolvable about the longitudinal axis of tube 110. As shaft 130 rotates, causing inner blade 140 to revolve about the longitudinal axis, inner blade 140 cooperates with outer blade 120 to create a rotational cutting action between the blades.

Surgical instrument 100 preferably includes a handle 150. As shown in FIG. 2A, handle 150 includes an elongated grip 152. Handle 150 can be configured to provide an ergonomic holding and controlling location for the operator of surgical instrument 100. Handle 150 is operatively associated with the proximal ends of tube 110 and tubular shaft 130.

Also, handle 150 provides a body on which a cutting control 151 can be disposed. Cutting control 151 can be configured, as described in further detail below, such that the operator of surgical instrument 100 can selectively revolve inner cutting blade 140 to perform the cutting of body tissue during surgery. Also as described in further detail below, control 151 can be operatively associated with either tube 110 or shaft 130 to move either inner cutting blade 140 or outer cutting blade 120, or both, with respect to the other.

Surgical instrument 100, as shown in FIG. 2A, can also be adapted for use as an electrocautery cutting tool. Either one of the outer blade 120 or inner blade 140, or both, can be adapted to be electrically energized. Electrical connector 160 can be provided extending from handle 150, for example, to provide a connection to a source of electricity (not shown). In the case of the surgical instrument 100 having electrically energized inner and outer blades, an inner insulating sleeve 136 is provided to electrically isolate tube 110 from shaft 130. An outer insulating sleeve (not shown) can also be provided to electrically isolate tube 110 from the body of the patient or from other instruments with which tube 110 might come into contact during the surgical procedure. The insulating sleeves can be made of a non-conductive material such as plastic.

In the case where one of either outer blade 120 or inner blade 140 is electrically energized, the surgical instrument 100 is a monopolar cutting tool having rotational cutting blades (i.e. a monopolar rotational cutting tool). When both outer blade 120 and inner blade 140 are electrically energized, the surgical instrument 100 is a bipolar rotational cutting tool. In either case, surgical instrument 100 can be used to cut and ligate blood vessels in a single step without the need for other tools or other process steps such as suturing, clipping, or the like.

During use, as inner blade 140 is revolved such that inner blade cooperates with outer blade 120, the body tissue disposed between outer blade 120 and inner blade 140 is cut by the mechanical rotational cutting action of the two blades and can be, at the same time, electrically cauterized. If the tissue being cut is a body vessel, for example, the vessel is simultaneously ligated by the electrocautery feature, if provided, of the rotational cutting tool. In use, surgical instrument 100 is inserted into an incision previously made in the patient. Distal end 102 of the instrument 100 is inserted into the incision and can be either inserted through a trocar sheath or directly into the patient.

FIG. 2B shows a cross-sectional view of surgical instrument 100. Surgical instrument 100 includes cutting control 151 on handle 150. Handle 150 includes a housing 153 having a longitudinal, cylindrical extension 159. Housing 153 includes grip 152. In the example shown in FIG. 2B, cutting control 151 includes shaft controller body 156 and ring 157 rotatably mounted on cylindrical extension 159. Ring 157 is coupled to shaft 130. Alternatively, cutting control 151 may be a lever coupled to shaft 130 and extending radially from shaft 130 through housing 153. Cutting control 151 can also be a knob, handle, or the like. Cutting control 151 is actuated by the operator by rotating shaft controller 156 or moving a lever (not shown) such that torque is applied to shaft 130 to rotate shaft 130 about its longitudinal axis.

FIG. 2B shows handle 150 including a seal 162 at the most proximal end of housing 153 around opening 158b. Seal 162 can be provided such that housing 153 and tube 110 operate as a secondary trocar. An auxiliary instrument 170, such as an endoscope, an irrigation or suction cannula, or a grasper can be inserted through opening 158b while seal 162 prevents fluids from exiting the body through lumen 138 and opening 158a and 158b of handle 150. Also, seal 162 can stop air or contaminants from entering the interior of instrument 100 from the outside.

FIG. 2C is a cross-sectional view of cutting control 151 of FIG. 2B. FIG. 2C shows ring 157 mounted rotatably around the cylindrical extension 159 of housing 153 (FIG. 2B). As described in further detail below, an opening 158a extends through cylindrical extension 159, and an auxiliary instrument 170 can be inserted through opening 158a.

Referring again to FIG. 2B, tube 110 is fixedly attached to handle 150 and shaft 130 rotatable relative to tube 110. Alternatively, shaft 130 can be fixedly attached to handle 150 and tube 110 can be rotatable about its longitudinal axis relative to shaft 130. In this case, cutting control 151 can be configured to be a tube controller.

Handle 150 of FIG. 2B includes housing 153 that is generally hollow and defines openings 158a and 158b. Opening 158a is located at the distal end of housing 153 and extends through cylindrical extension 159. Opening 158b is located at the proximal end 103 of housing 153. Opening 158a is in communication with lumen 138 of tubular shaft 130. Openings 158a, 158b, and lumen 138 provide access through the instrument 100 to the distal end 132 of tubular shaft 130. An auxiliary instrument 170 can be inserted through opening 158 and further through lumen 138. Examples of an auxiliary instrument 170 are a suction or irrigation cannula, an imaging device, or a sensor.

The distal end 102 of surgical instrument 100 has a diameter D, as shown in FIG. 2B. The diameter D of the distal end 102 can be sized such that body vessels of many sizes may be cut. The surgical instrument 100 rotationally cuts body tissue without disturbing surrounding tissue that is outside the circumference of the tool. The rotational blades of surgical instrument 100 do not expand or spread beyond the circumference defined by diameter D.

Figure 1:
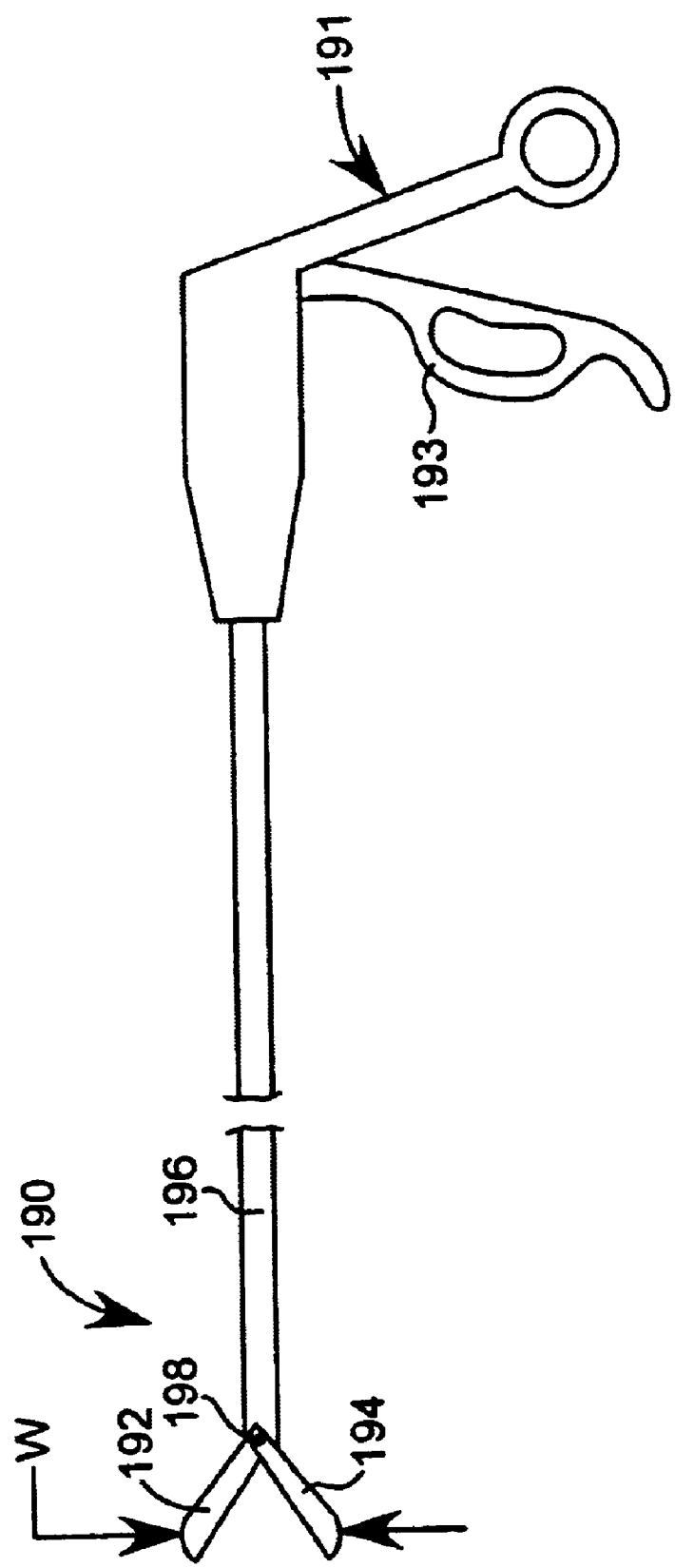
FIG. 1 is a side view of prior art surgical scissors.

In contrast, the pivoting blades of the scissors 190 of FIG. 1 must be spread apart in order to be positioned around the tissue to be cut. When the blades of the scissors 190 are spread apart, the surrounding tissue can be damaged. Surgical instrument 100 does not cause as much damage to surrounding tissue because its rotational blades are rotated within a fixed circumference rather than spread apart. Also, the rotational cutting tool design of the example of FIGS. 2A and 2B provides a better feel and control of the cutting action for the operator of the instrument because of the direct control of the rotating blade through the cutting controller 151.

Referring again to FIGS. 2A and 2B, tube 110 and shaft 130 are coaxial, having a common longitudinal axis 119. As described with reference to FIGS. 2A and 2B, tube 110 and shaft 130 can be rotated about axis 119 (FIG. 2B) to perform the rotational cutting. Shaft 130 is rotatably disposed within tube 110 such that the outer surface of shaft 130 is in close proximity to the inner surface of tube 110. Since inner blade 120 and outer blade 140 extend longitudinally from tube 110 and shaft 130, respectively, the blades also become closely proximate to each other when either tube 110 or shaft 130 is rotated relative to the other. The rotational cutting action of the blades is described in further detail below.

FIGS. 2A and 2B show one embodiment of the invention in which the tube 110 and shaft 130 are coaxial. The rotational cutting action of the surgical instrument of the invention does not require that the tube 110 and shaft 130 be coaxial, however. The rotational cutting action is performed by one blade revolving about a longitudinal axis with respect to another blade. The revolving blade need not extend from a coaxial tube or shaft, as described below with reference to FIG. 3.

FIG. 3 shows another embodiment of a surgical instrument 200 of the invention. Instrument 200 includes tube 210 and shaft 230 within tube 210. Shaft 230 is shown in FIG. 3 as being solid, but can alternatively be tubular. Tube 210 has a first axis 219 and shaft 230 has a second axis 239. The axes of the tube 210 and shaft 230 are displaced from each other. Tube 210 includes an outer blade 220 extending longitudinally from its distal end 212. Likewise, shaft 230 includes an inner blade 240 extending longitudinally from its distal end 232. Inner blade 240 and outer blade 220 operate in a similar fashion as the embodiment previously described with respect to FIGS. 2A and 2B.

In FIG. 3, however, shaft 230 is fixedly attached to handle 250 while tube 210 is rotatable about its axis with respect to handle 250 and shaft 230. That is, while shaft 230 including inner blade 240 remain fixed relative to handle 250, tube 210 can be rotated by rotating cutting control 251 which is coupled to tube 210. When cutting control 251, and thus tube 210 including inner blade 220, is rotated, outer blade 220 and inner blade 240 become operatively engaged so as to cut the body tissue (not shown) that is located between the outer blade 220 and inner blade 240. The body tissue to be cut is situated transversely between the blades by the operator of surgical instrument 200 by moving the instrument into position as desired.

In an alternate embodiment, tube 210 can be fixed and shaft 230 can be revolvable about longitudinal axis 239. Yet another embodiment of a surgical instrument 200 can include a tube 210 rotatable about axis 219 and a shaft 230 revolvable about axis 219.

Handle 250 of FIG. 3 can define opening 258 so that an auxiliary instrument (not shown) can be inserted through surgical instrument 200, as similarly described with respect to the instrument of FIG. 2B. Handle 250 includes a cylindrical extension 259 through which opening 258 is defined. Cutting control 251 is a tube controller 254 that is coupled to tube 210. It should be noted that tube controller 254 can comprise ring 255 rotatably disposed and surrounding extension 259 as shown in FIG. 3. Alternatively, tube controller 254 can be a lever (not shown) fixedly attached to tube 210.

Figure 4:
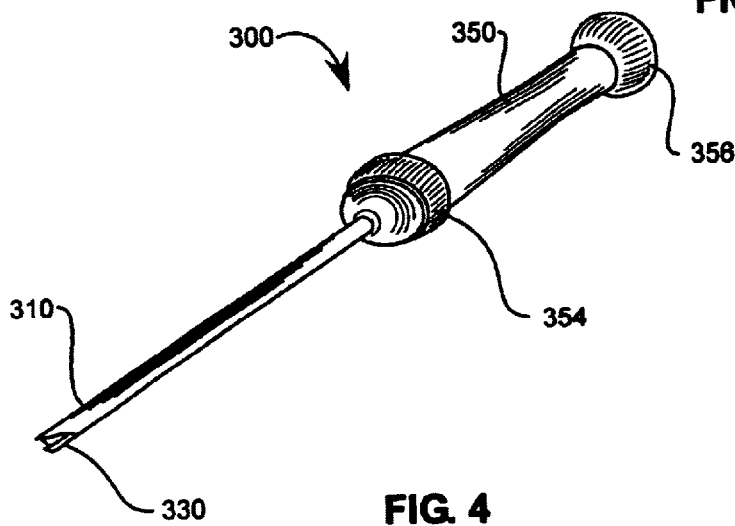
FIG. 4 is a perspective view of a surgical instrument in accordance with another alternate embodiment of the invention.

FIG. 4 shows with another embodiment of a surgical instrument 300 of the invention. Surgical instrument 300 also includes tube 310 and shaft 330. Shaft 330 can be either tubular and coaxial, similar to shaft 130 of FIG. 2B, or can have an axis displaced from the axis of tube 310, similar to shaft 230 of FIG. 3. In either case, FIG. 4 shows a surgical instrument 300 having a handle 350 that includes two tube controllers 354 and 356. The two tube controllers allow the operator of the instrument 300 to rotate the tube 310 from at least two hand position.

In any of the embodiments described herein, the tube and the shaft are rotatable with respect to each other such that the inner blade is revolvable about the central axis of the distal end of the instrument, which generally (i.e., within manufacturing tolerances) corresponds to the central longitudinal axis of the tube. Within the rotating mechanism, detents or a frictional mechanism can be provided to hold the tube or shaft in position once the operator rotates the tube or shaft.

Figure 5:
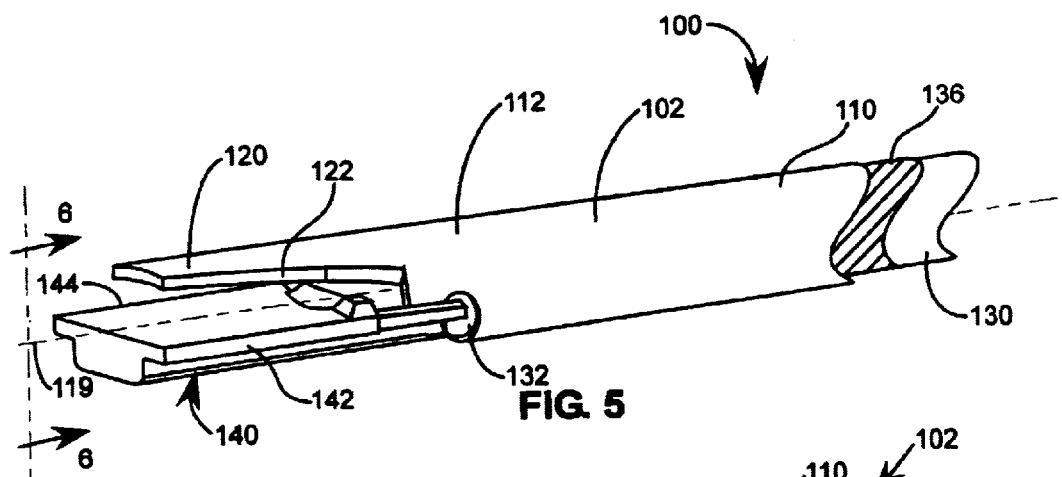
FIG. 5 is an enlarged partial view of the rotational cutting blades of the surgical instrument of FIG. 2A.

FIG. 5 shows an embodiment of the distal end 102 of the surgical instrument 100. Tube 110 includes outer blade 120 at its distal end 112. Outer blade 120 extends longitudinally from distal end 112 of tube 110. As shown in FIG. 5, outer blade 120 is an extension of the wall of tube 110. Outer blade 120 need not be integral with tube 110, however. Outer blade 120 can be a separate piece that is either fixedly or removably attached to distal end 112 of tube 110. Inner blade 140 can be similarly attached to shaft 130 or can be integral with shaft 130. When outer blade 120 or inner blade 140 are removable, they can be replaced with new inner or outer blades that can have different shapes or configurations.

Outer blade 120 includes a first outer cutting edge 122 and a second outer cutting edge 124 (shown in FIG. 6) on the opposite lateral edge of outer blade 120. The first and second outer cutting edges are laterally disposed on either side of outer blade 120 and, in the example shown in FIG. 5, extend longitudinally from tube 110.

FIG. 5 also shows shaft 130 coaxially located within tube 110. Insulating sleeve 136 can be provided between tube 110 and shaft 130 to electrically isolate tube 110 from shaft 130 when either or both are electrically energized. Inner blade 140 extends longitudinally from distal end 132 of shaft 130. Outer blade 120 and inner blade 140 are operatively associated such that they have a rotational cutting action.

Inner blade 140 has a first inner cutting edge 142 and a second inner cutting edge 144. When shaft 130 is rotated within tube 110, inner blade 140 revolves about the longitudinal axis 119 of tube 110. Thus, as inner blade 140 is revolved to bring first inner cutting edge 142 into operative contact with first outer cutting edge 122, the two cutting edges contact each other at a moving cutting point beginning closest to the most proximal end of the intersection of the cutting edges. As the inner blade 140 revolves further in the counter-clockwise direction as viewed from the end of instrument 100 in FIG. 5, the cutting point moves distally along the engaged inner and outer cutting edges.

For illustrative purposes, outer blade 120 and inner blade 140 are shown having first and second cutting edges. It should be noted, however, that each blade can be provided with only one cutting edge in an alternate embodiment.

Figure 6:
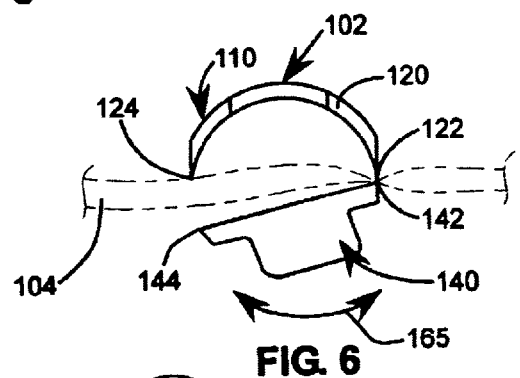
FIG. 6 is an end view of the instrument of FIG. 5 taken along line 6—6 of FIG. 5.

FIG. 6 illustrates the cutting of a vessel or body tissue 104 at the distal end 102 of the instrument. In the example of FIG. 6, inner blade 140 is revolvable in the direction of the arrows 165 as the shaft is rotated about the longitudinal axis of the tube 110. Outer blade 120 remains stationary in the example of FIG. 6. First outer cutting edge 122 and first inner cutting edge 142 are shown in the cutting position. Second outer cutting edge 124 and second inner cutting edge 144 are shown in a separated or open position.

The surgical instrument 100 can provide two inner and two outer cutting edges as illustrated in FIGS. 5 and 6 so that the operator can select the location of the cut of the body tissue 104 without rotating the entire instrument 180 degrees. In an alternate embodiment, second outer cutting edge 124 and second inner cutting edge 144 can be replaced by inner and outer clamping surfaces. In yet another alternate embodiment, one of the inner or outer cutting edges can be replaced by an anvil such that the respective 10 outer or inner cutting edge cuts the body tissue by being forced against the anvil.

FIGS. 7–13 illustrate various different embodiments of the distal end of the surgical instrument of the invention.

FIGS. 7A and 7B show distal end 402 including tube 410 having a distal end 412 and an outer blade 420 extending longitudinally from distal end 412. Inner blade 440 is also shown in FIGS. 7A and 7B.

FIG. 7A shows outer blade 420 having a first outer cutting edge 422. First outer cutting edge 422 of the example of FIG. 7A is formed, for example, by making a curved cut transversely across tube 410. The curve formed by first outer cutting edge 422 follows a point that travels longitudinally along the surface of tube 410 while also traveling spirally around tube 410. Likewise, second outer cutting edge (not shown) follows a curve that is symmetrical to that of first outer cutting edge 422.

FIG. 7B shows inner blade 440 having a generally semicircular cross section. The chord of the cross section of inner blade 440 travels through or near the central axis of the tube 410. Inner blade 440, as shown in FIG. 7A, extends generally longitudinally from the shaft (not shown) similarly to previously described embodiments. Inner blade 440 includes first inner cutting edge 442 and second inner cutting edge 444. First inner cutting edge 442 is operatively associated with first outer cutting edge 422, and second inner cutting edge 444 is operatively associated with second outer cutting edge 424.

FIGS. 8A and 8B show yet another embodiment of a distal end 502 of a surgical instrument of the invention. Inner blade 540 extends longitudinally from a shaft (not shown) similarly to previously described embodiments. As shown in FIG. 8B, inner blade 440 has a generally rectangular cross section. Inner blade 540 also revolves around a central axis. First inner cutting edge 542 and second inner cutting edge 544 are located on the outer-most corners of the rectangular cross section of inner blade 540. As observed from the end of distal end 502, the cutting edges of inner blade 540 follow the inner circumference of tube 510 when inner blade 540 is revolved around the central axis. In this manner, inner blade 540 cooperatively engages outer blade 520 to provide the rotational cutting action.

FIGS. 9A and 9B show still another embodiment of a distal end 602 of a surgical instrument of the invention. Inner blade 640, as shown in FIG. 9A, extends generally longitudinally from a shaft (not shown). Inner blade 640 has a first inner cutting edge 642 and a second inner cutting edge 644. First and second cutting edges 642 and 644 extend longitudinally along inner blade 640 and toward each other at the distally terminal point of blade 640 to form a roughly triangular profile.

FIG. 9B shows an end view of distal end 602. Inner blade 640 is shown in FIG. 9B as having a somewhat rectangular cross section. Inner blade 640 has first inner cutting edge 642 and second inner cutting edge 644 disposed at its outer-most corners. Inner blade 640 of FIGS. 9A and 9B revolves around the longitudinal axis of the tube 610, in a similar fashion as previously described embodiments.

FIGS. 10A–10C show another embodiment of a distal end 702 of a surgical instrument of the invention. Tube 710 includes distal end 712 from which outer blade 720 longitudinally extends. As shown in FIG. 10B, the outer blade includes a first cutting edge 722 that has a curved profile that can be formed by cutting trarversely across tube 710.

FIGS. 10A–10C show inner blade 740. As shown in FIG. 10C, inner blade 740 has a partial-circular cross section. The chord of the cross section is displaced from and is transverse to the longitudinal axis of tube 710. As shown in FIG. 10C, inner blade 740 includes a first inner cutting edge 742 and a second inner cutting edge 744 at the points where the chord of the cross section meets the outer circumference of inner blade 740.

FIGS. 11A and 11B show still another embodiment of a distal end 802 of a surgical instrument of the invention. FIG. 11B shows outer blade 820 and inner blade 840 having arced cross sections which are each approximately a quarter of a circle.

FIGS. 12A and 12B show yet another embodiment of a distal end 902 of a surgical instrument of the invention. FIGS. 12A and 12B show outer blade 920 and inner blade 940, each extending at an angle away from the longitudinal axis of tube 910. The outwardly extending inner and outer blades of the embodiment of FIGS. 12A and 12B provide a larger space between the blades so that a larger piece of body tissue or a larger diameter body vessel can be cut.

FIGS. 13A and 13B show another embodiment of the surgical instrument of the invention having a distal end 180. Distal end 180 provides a configuration that can be used for biopsy collection. Distal end 180 includes an outer blade 181 which includes a first scoop 182. First scoop 182 has a first cutting edge 183. Inner blade 185 likewise includes a second scoop 186. Second scoop 186 has a second cutting edge 187. The first and second scoops are operatively associated to collect the biopsy sample when the shaft (not shown) is rotated within the tube 186.

FIG. 13A shows first cutting edge 183 and second cutting edge 187 being serrated. It should be noted that any of the cutting edges described herein can be serrated.

Figure 14A:
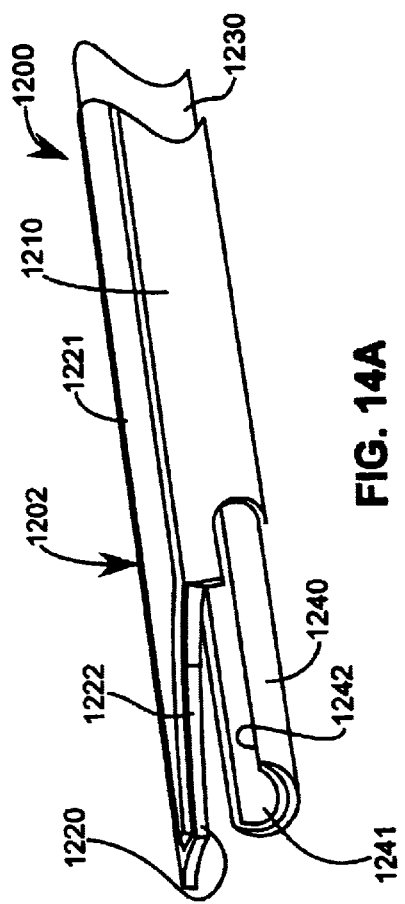
FIG. 14A is a partial perspective view of rotational cutting blades of another embodiment of the invention.
Figure 14B:
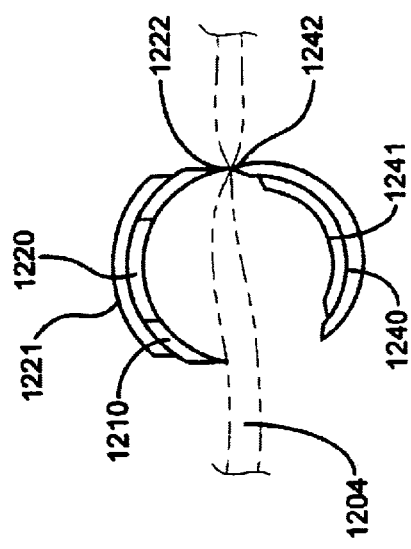
FIG. 14B is an end view of the rotational cutting blades of FIG. 14A.

FIGS. 14A and 14B show another embodiment of a surgical instrument 1200 of the invention having a distal end 1202. FIG. 14A shows tube 1210 having shaft 1230 within its lumen. Tube 1210 includes outer blade 1220 extending from its distal end, and shaft 1230 includes inner blade 1240 extending from its distal end. Outer blade 1220 has an outer cutting edge 1222, and inner blade 1240 has an inner cutting edge 1242.

Surgical instrument 1200 is a bipolar electrocautery instrument that includes rotational cutting features. The electric energy for electrocautery is provided through electrodes that are on the inner and outer blades, rather than through the blades themselves. The electrodes do not contact each other, but provide an electric potential in the vicinity of the cutting edges of the blades. In this configuration, the cutting edges of the inner and outer blades can contact each other to provide mechanical cutting action without causing an electrical short. At the same time, electrocautery can be provided by instrument 1200.

As shown in FIGS. 14A and 14B, an outer electrode 1221 is provided on the exterior surface of the outer blade 1220 and can be extended along the outer surface of the tube 1210. An inner electrode 1241 is provided on the inner surface of the inner blade 1240. Alternatively, electrodes can be provided on both inner and outer surfaces of each of the outer and inner blades. As shown in FIG. 14A, body tissue 1204 is cut by mechanical cutting action as outer cutting edge 1222 and inner cutting edge 1242 are rotated toward each other.

A dielectric or insulating material (not shown) is preferably provided between the outer electrode 1221 and the outer blade 1220. Similarly, a dielectric or insulating material is provided between the inner electrode 1241 and the inner blade 1240. The dielectric or insulating material can be an adhesive material that attaches the electrodes to the blades.

Figure 15:
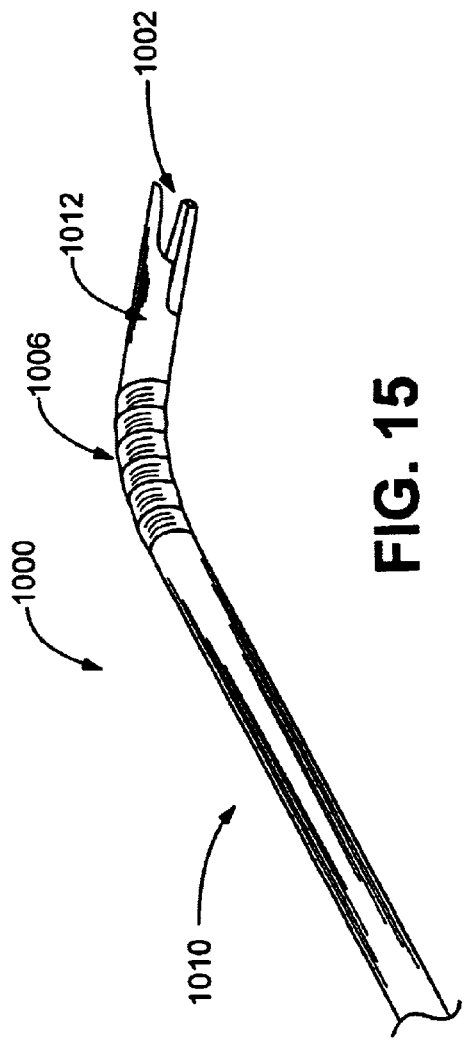
FIG. 15 is a partial perspective view of a surgical instrument of another embodiment of the invention.

FIG. 15 shows the distal end 1002 of another embodiment of a surgical instrument of the invention. Distal end 1002 includes a bendable section 1006 located slightly proximate to the distal end 1012 of tube 1010. The bendable section 1006 can be as short or as long along the length of the tube 1010 as desired for any particular application. For example, if the instrument 1000 is to be used in a part of a body of a patient that is particularly difficult to access, it is desirable to have tube 1010 as flexible along as much of its length as possible. The embodiment of the present invention exemplified by surgical instrument 1000 of FIG. 15 can incorporate an articulating mechanism (not shown) such that distal end 1002 can be moved transversely by controls on the handle of the instrument.

Figure 16:
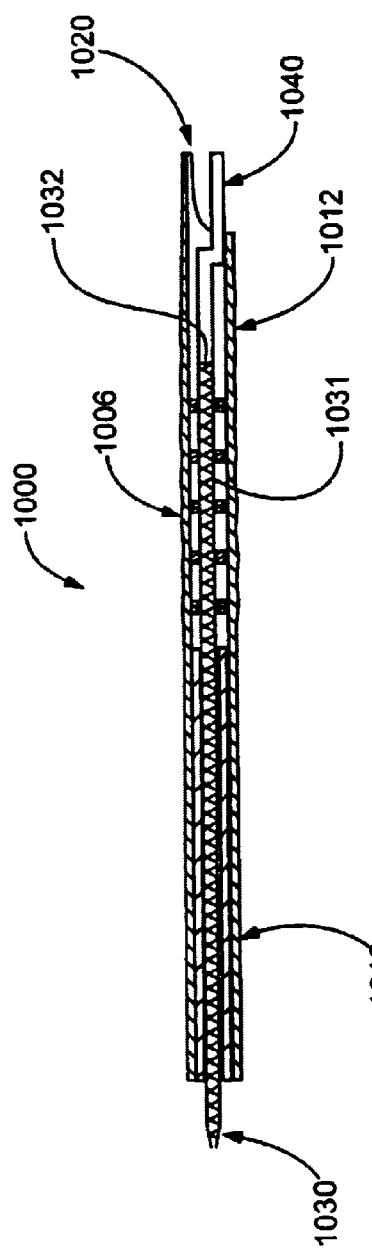
FIG. 16 is a sectional view of the surgical instrument of FIG. 15.

FIG. 16 shows an example of the bendable section 1006 of the instrument 1000 of FIG. 15. FIG. 16 shows tube 1010 having a distal end 1012 and an outer blade 1020 extending longitudinally from distal end 1012. Shaft 1030 is coaxial with tube 1010. Shaft 1030 includes inner blade 1040 attached at distal end 1032 of shaft 1030. Bendable section 1006 of tube 1010 can include a spiral wire (or spring-like) structure or a similar tubular structure that is flexible. Within bendable section 1006, the example of FIG. 16 shows shaft 1030 including several hinged sections 1031. Shaft 1030 can also be bendable in the vicinity of bending region 1006 without having hinged sections.

FIG. 17 shows another embodiment of a surgical instrument 1100 of the invention. Surgical instrument 1100 includes a rotational cutting blade at its distal end 1102. Also, instrument 1100 includes a tube 1110 that is telescopic. Instrument 1100 also includes a shaft (not shown) within tube 1110 that is also telescopic.

FIG. 18 shows instrument 1100 of FIG. 17 having a telescopic tube 1110. FIG. 18 shows shaft 1130 within tube 1110 and extending through handle 1150. Shaft 1130 of instrument 1100 is also telescopic.

The instrument of the present invention can be made from materials that are commonly used for surgical instruments. For example, the tube and the shaft including the outer and inner blades as previously described can be made of stainless steel. The tube and shaft can also be made of plastic. The handle can be made of plastic or steel. The tubular shape of the tube and tubular shaft allows the instrument to easily withstand the torque applied to rotate the tube or shaft.

Also, the tubular design allows for other auxiliary instruments to be used together with the surgical instrument of the invention. An auxiliary instrument can be slidably inserted through the handle and lumen of the tubular shaft either before or during the surgery. For example, an endoscope can be inserted through the instrument so that the surgeon can observe the body cavity in front of the instrument as he inserts the instrument into the patient's body. After the instrument is placed as desired, the endoscope can be removed and another instrument, such as a suction or irrigation cannula can replace the endoscope. Thus, fewer incisions need to be made, which is beneficial to the patient.

The present invention also includes a method for cutting body tissue. The method includes inserting a surgical instrument including a tube having a distal end, a proximal end, and a longitudinal axis between the distal and proximal ends into the patient's body. The instrument further includes an outer blade at the distal end of the tube. The instrument also includes a shaft having a distal end, a proximal end, and an inner blade at the distal end of the shaft. As previously described with respect to the various embodiments of the apparatus of the invention, the shaft is rotatably disposed within the tube. Rotation of the shaft with respect to the tube, or rotation of the tube with respect to the shaft, results in revolving the inner blade about the central axis of the tube. As the inner blade revolves about the central axis, the inner and outer blades are rotatably engaged.

The method further includes aligning body tissue that has been selected to be cut between the inner and outer blades of the instrument. Next, the tube (or the shaft) is rotated about the longitudinal axis such that the inner and outer blades engage to cut the body tissue. The method can further include electrically energizing at least one of the inner and outer blades wherein the body tissue can be cauterized during cutting.

The method and apparatus described herein can be used in a variety of surgical procedures. For example, saphenous vein harvesting is one procedure that can be improved by the use of a rotational scissors that incorporates electrocautery. The method and apparatus of the invention can be used at other locations such as, for example, around the femoral artery or the illiac artery. Still other surgeries that can be performed using the apparatus and method of the present invention include surgeries of the gall bladder or hernias.

It should be noted that the embodiments of the method and apparatus described herein are exemplary of the present invention and are not to be construed as limiting the scope of the invention.

What is claimed is:

1. A surgical instrument comprising:
   a tube having a distal end and a proximal end, said distal end including a first cutting edge; and
   a shaft within said tube, said shaft having a distal end and a proximal end, said distal end of said shaft including a blade, one of said shaft and said tube being rotatable with respect to the other such that said blade cooperates with said cutting edge wherein said blade has an elongated portion having two opposing surfaces and a second cutting edge on each of said opposing surfaces.

2. The instrument of claim 1 wherein said shaft is coaxial with said tube.

3. The instrument of claim 2 wherein said shaft has an inner lumen.

4. The instrument of claim 2 wherein said shaft has an inner lumen such that an imaging device may be inserted therein.

5. The instrument of claim 2 wherein said shaft has an inner lumen such that a separate surgical instrument may be inserted therein.

6. The instrument of claim 1 wherein one of said first cutting edge and said blade is adapted to be electrically energized.

7. The instrument of claim 1 wherein said tube is fixedly attached to a handle and said shaft is rotatable relative to said tube.

8. The instrument of claim 1 wherein said blade includes a serrated cutting edge.

9. The instrument of claim 1 wherein said first cutting edge on said tube is serrated.

10. A surgical instrument comprising:
    a handle;
    a tube extending from and coupled to said handle, said tube having a distal end and a first cutting edge at said distal end, said tube having a proximal end associated with said handle;
    a tubular shaft defining a lumen coaxial with said tube, said shaft rotatably disposed within said tube and having at its distal end an elongated portion having two opposing surfaces and a second cutting edge on each of said opposing surfaces, said opposing surfaces having an insulating layer thereon, said shaft having a proximal end adjacent said handle and a distal end adjacent said distal end of said tube, wherein one of said second cutting edges on said shaft and said first cutting edge on said tube is adapted to be electrically energized; and
    wherein said handle defines an opening in communication with said lumen of said tubular shaft wherein said opening and said lumen provide access through the instrument to said distal end of said tubular shaft.

11. The instrument of claim 10 wherein said tube and said shaft are bendable.

12. A surgical instrument comprising:
    a handle;
    a tube having a distal end and an outer blade extending from said distal end, said tube having a proximal end associated with said handle; and
    a shaft disposed within said tube, said shaft having a distal end adjacent said distal end of said tube, said shaft having an inner blade extending from said distal end, wherein said inner blade has an elongated portion having two opposing surfaces and a cutting edge on each of said opposing surfaces, said opposing surfaces having an insulating layer thereon, said shaft having a proximal end extending into said handle, wherein said inner blade and said outer blade are adapted to be electrically energized.

13. The instrument of claim 12 wherein said tube has a first longitudinal axis and said shaft has a second longitudinal axis displaced from said first longitudinal axis.

14. The instrument of claim 13 wherein said tube is fixedly attached to said handle and said shaft is revolvable about said first longitudinal axis relative to said tube.

15. The instrument of claim 13 wherein said shaft is fixedly attached to said handle and said tube is rotatable about said first longitudinal axis relative to said shaft.

16. The instrument of claim 13 wherein said shaft is revolvable about said first longitudinal axis relative to said tube, and said tube is rotatable about said first longitudinal axis relative to said shaft.

17. A method for cutting body tissue, the method comprising:

inserting a surgical instrument comprising a tube having a distal end, a proximal end, a longitudinal axis between said distal and proximal ends, and a first cutting edge at said distal end of said tube, said instrument further including a shaft having a distal end, a proximal end, and a blade at said distal end of said shaft, wherein said blade has an elongated portion having two opposing surfaces and a second cutting edge on each of said opposing surfaces, said shaft being rotatably disposed within said tube such that said cutting edge and said blade are rotatably engageable;

aligning the body tissue to be cut between said first cutting edge and said blade; and rotating at least one of said tube and said shaft about said longitudinal axis such that said first cutting edge and said blade engage to cut the body tissue.

18. The method of claim 17 further comprising electrically energizing at least one of said first cutting edge and said blade wherein the body tissue is cauterized.

* * * * *